US00PP25525P3

(12) United States Plant Patent
Bentley

(10) Patent No.: US PP25,525 P3
(45) Date of Patent: May 5, 2015

(54) ***LAVANDULA* PLANT NAMED 'IBPR910-2'**

(50) Latin Name: *Lavandula stoechas*
Varietal Denomination: IBPR910-2

(71) Applicant: Howard Bentley, Wonga Park (AU)

(72) Inventor: Howard Bentley, Wonga Park (AU)

( * ) Notice: Subject to any disclaimer, the term of this patent is extended or adjusted under 35 U.S.C. 154(b) by 97 days.

(21) Appl. No.: 13/815,339

(22) Filed: Feb. 22, 2013

(65) Prior Publication Data

US 2014/0245514 P1 Aug. 28, 2014

(51) Int. Cl.
*A01H 5/00* (2006.01)

(52) U.S. Cl.
USPC ..... Plt./445

(58) Field of Classification Search
USPC ..... Plt./445
See application file for complete search history.

(56) References Cited

PUBLICATIONS

PLUTO Plant Variety Database search for IB 910-2 pp. 1-2.*
PLUTO Plant Patent Variety Database Oct. 30, 2014. p. 1.*

* cited by examiner

*Primary Examiner* — Annette Para
(74) *Attorney, Agent, or Firm* — Cassandra Bright

(57) ABSTRACT

A new and distinct *Lavandula* cultivar named 'IBPR910-2' is disclosed, characterized by a long flowering season and dense plant habit. The new variety can also be characterized by long and wide infertile bracts of strong iridescent pink coloration and short peduncle length. The new variety is a *Lavandula*, normally produced as an outdoor garden or container plant.

1 Drawing Sheet

Latin name of the genus and species: *Lavandula stoechas*.
Variety denomination: 'IBPR910-2'.

BACKGROUND OF THE INVENTION

The new *Lavandula* cultivar is a product of a planned breeding program conducted by the inventor, Howard Bentley, in Wonga Park, Australia. The objective of the breeding program was to produce new *Lavandula* varieties for ornamental commercial applications. The cross resulting in this new variety was made during October of 2008.

The parent varieties are both proprietary, undistributed seedlings from the inventor's own breeding program. The new variety was first selecteded in September of 2009 by the inventor in a group of seedlings resulting from the 2008 crossing, in a research greenhouse in Wonga Park, Australia.

Asexual reproduction of the new cultivar was performed by vegetative cuttings. This was performed at a research greenhouse in Wonga Park, Australia in September of 2009 and has shown that the unique features of this cultivar are stable and reproduced true to type through at least 6 successive generations.

SUMMARY OF THE INVENTION

The cultivar 'IBPR910-2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IBPR910-2' These characteristics in combination distinguish 'IBPR910-2' as a new and distinct *Lavandula* cultivar:

1. Strong iridescent pink infertile bract coloration.
2. Long length and width of infertile bracts.
3. Dense plant habit.
4. Long flowering season.
5. Short peduncle length.

Plants of the new cultivar 'IBPR910-2' are similar to plants of the seed parent, in most horticultural characteristics, however, plants of the new cultivar 'IBPR910-2' produce longer, wider and greater iridescent pink infertile bracts coloration than those of the seed parent. 'IBPR910-2' is also a plant with greater vigor and larger mature size than the seed parent.

Plants of the new cultivar 'IBPR910-2' are similar to plants of the pollen parent; in most horticultural characteristics, however, plants of the new cultivar 'IBPR910-2' produce wider infertile bracts. Additionally, plants of the new variety have a denser growth habit as well as a longer flowering season than the pollen parent.

COMMERCIAL COMPARISON

Plants of the new cultivar 'IBPR910-2' are comparable to the variety *Lavandula* 'Sweetberry Ruffle' U.S. Plant Pat. No. 22,447. The two *Lavandula* varieties are similar in most horticultural characteristics; however, the new variety IBPR910-2' differs in producing longer peduncles and stronger iridescent pink coloration of the infertile bracts that the comparator. Additionally 'IBPR910-2' produces a plant of stronger vigor and larger mature size as well as longer inflorescence than the comparator.

Plants of the new cultivar 'IBPR910-2' can also be compared to the commercial variety *Lavandula* 'Strawberry Ruffles' U.S. Plant Pat. No. 22,490. These varieties are similar in most horticultural characteristics; however 'IBPR910-2' produces wider infertile bracts of stronger iridescent pink coloration as well as longer peduncles than those of the comparator. Additionally 'IBPR910-2' produces a plant of stronger vigor and denser plant habit than the comparator.

BRIEF DESCRIPTION OF THE PHOTOGRAPH

The accompanying photograph in FIG. 1 illustrates in full color a typical plant of 'IBPR910-2' grown outdoors in Australia. Age of the plant photographed is approximately 40 weeks from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'IBPR910-2' plants grown outdoors during, Spring, summer, autumn in Wonga Park, Australia. The growing temperature ranged from 20° C. to 35° C. during the day and from 15° C. to 25° C. during the night. General light conditions are bright, normal sunlight. Measurements and numerical values represent averages of typical plant types.

Botanical classification: *Lavandula stoechas* 'IBPR910-2'.

PROPAGATION

Time to initiate roots: About 10-14 days at approximately 21° C.

Time to produce a rooted cutting: About 25-35 days at 21° C.

PLANT

Age of plant described: Approximately 40 weeks from rooted cutting.

Plant spread: Approximately 70 cm.

Plant height: Approximately 50 cm, to top of flowering plane. Approximately 40 cm to top of foliar plane.

Growth rate: Moderate to fast.

Length of primary lateral branches: Approximately 30 cm.

Diameter of lateral branches: Approximately 0.4 cm.

Quantity of lateral branches: About 40.

Plant habit: Dense to very dense.

Stem:

- *Juvenile color*.—Near Yellow-Green group RHS 145A.
- *Semi-ripe color*.—Near Grey-Brown group RHS N199D.
- *Mature color*.—Near Grey-Brown group RHS N199C.
- *Texture/pubescence*.—Pubescent (when Juvenile).

Internode length: Approximate 1.5 cm. (semi-ripe lateral stem).

FOLIAGE

Leaf:

- *Arrangement*.—Opposite.
- *Leaf type*.—Simple.
- *Quantity*.—Approximately 26 per main branch.
- *Average length*.—Approximately 2.6 cm. (range 4 cm to 1 cm).
- *Average width*.—Approximately 0.37 cm. (range 0.6 cm to 0.2 cm).
- *Shape of blade*.—Oblong elongated.
- *Apex*.—Acute.
- *Base*.—Truncate.
- *Attachment*.—Sessile.
- *Margin*.—Entire.
- *Texture of surfaces*.—Pubescent.
- *Leaf fragrance*.—Resinous scent.
- *Color*.—Young foliage upper side: Near Green group RHS 138B. Young foliage under side: Near Green group RHS 138B. Mature foliage upper side: Near Green group RHS 138A. Mature foliage under side: Near Green group RHS 138B.
- *Venation*.—Type: Reticulate. Venation color upper side: Near Green group RHS 138B. Venation color under side: Near Green group RHS 138B.
- *Petiole*.—Absent.

FLOWER

Bloom period: Main Flush late winter to late spring. Spot flowering occurs throughout Summer and Fall.

Inflorescence:

- *Form*.—Small single flower in verticillasters arranged in spikes. 4 to 12 rows of flowers. Flowers have small bracts, and large showy terminal bracts. Number of individual flowers per spike: Approximately 80 to 100. Corolla shape: Salverform. Petal Number: 5. Petals Fused or Unfused: Fused at base. Petal Shape: Top 2 lobes obovate, lower 3 lobes ovate. Petal Margin: Entire. Petal Surfaces: Glabrous. Length: Approximately 0.73 cm. (corolla tube). Diameter: Approximately 0.45 cm.
- *Inflorescence size, excluding terminal bracts*.—Length: Approximately 4.2 cm. Width: Approximately 2.5 cm. Shape: Cylindrical. Coloration of individual flowers and entire spikes, excluding terminal bracts: Immature: Near Purple group RHS 77B. Mature: Near Purple group RHS 77A. Fading: Near Purple group RHS 79C. Calyx Width: 0.23 cm. Calyx Length 0.75 cm. Calyx Shape: Tubular. Calyx color: RHS Green group 138B. Bract shape: Orbicular. Bract apex: Cuspidate. Bract Color: Near Green group RHS 138B and Near Greyed-Purple group RHS 187B.

Terminal bracts (sterile):

- *Quantity*.—Usually 4 per inflorescence.
- *Length*.—Approximately 4.5 cm.
- *Width*.—Approximately 2.9 cm.
- *Form*.—Petaloid.
- *Margin*.—Entire and undulating.
- *Surface*.—Smooth.
- *Appearance*.—Iridescent Pink.
- *Shape*.—Broadly oblanceotale.
- *Apex*.—Broadly Acute.
- *Base*.—Obtuse.
- *Vein pattern*.—Reticulate.
- *Duration on plant*.—Approximately 12 weeks, with good color. Persistent.

Fragrance: Resinous scent.

REPRODUCTIVE ORGANS

Not available at the time of description

OTHER CHARACTERISTICS

Seeds and fruits: Not observed to date.

Disease/pest resistance: More resistant to leaf fungal problems in higher humidity environments than other know varieties of *Lavandula stoechas*.

What is claimed is:

1. A new and distinct cultivar of *Lavandula* plant named 'IBPR910-2' as herein illustrated and described.

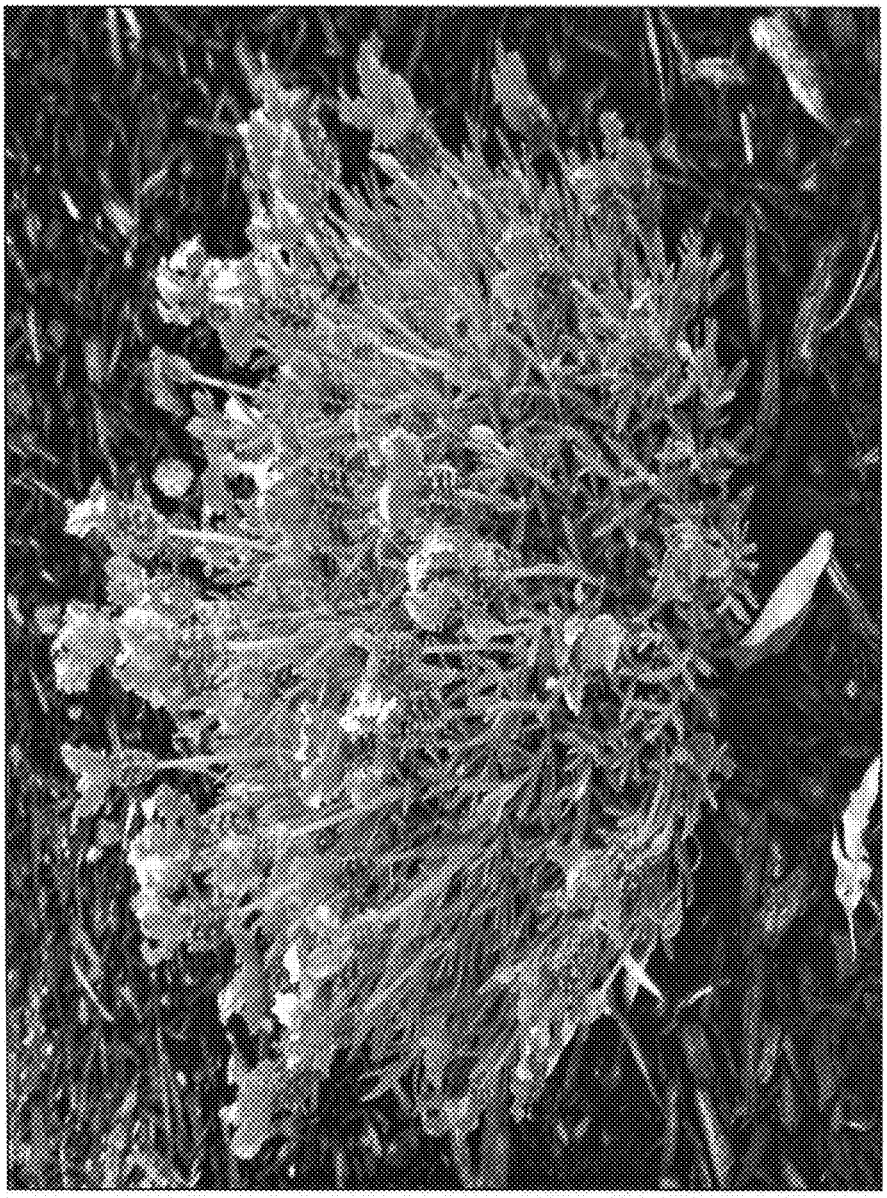

* * * * *